United States Patent [19]
Thompson et al.

[11] Patent Number: 5,814,024
[45] Date of Patent: Sep. 29, 1998

[54] NEEDLELESS VALVE

[75] Inventors: John Thompson, San Clemente, Calif.; David Ziv, Hagalil, Israel

[73] Assignee: Elcam Plastics, Hagalil, Israel

[21] Appl. No.: 757,156

[22] Filed: Nov. 27, 1996

[51] Int. Cl.$^6$ .................................................. A61M 5/00
[52] U.S. Cl. ........................... 604/246; 604/86; 604/256; 251/149.1
[58] Field of Search ................................ 604/246, 247, 604/82, 83, 86, 88, 89, 167, 169, 280, 283, 256; 251/149.1

[56] References Cited

U.S. PATENT DOCUMENTS

| | | | |
|---|---|---|---|
| 3,831,629 | 8/1974 | Mackal et al. | 137/525 |
| 3,853,127 | 12/1974 | Spademan | 128/214.4 |
| 3,896,853 | 7/1975 | Bernhard | 137/614.05 |
| 4,051,852 | 10/1977 | Villari | 128/278 |
| 4,512,766 | 4/1985 | Vailancourt | 604/169 |
| 4,666,429 | 5/1987 | Stone | 604/83 |
| 4,681,132 | 7/1987 | Lardner | 137/271 |
| 4,683,916 | 8/1987 | Raines | 137/854 |

(List continued on next page.)

FOREIGN PATENT DOCUMENTS

| | | |
|---|---|---|
| 0 569 030 | 11/1993 | European Pat. Off. . |
| 0 684 050 | 11/1995 | European Pat. Off. . |
| 92/04936 | 4/1992 | WIPO . |
| WO 93/05838 | 4/1993 | WIPO . |
| WO 93/05839 | 4/1993 | WIPO . |
| WO 93/11828 | 6/1993 | WIPO . |
| 96/00107 | 1/1996 | WIPO . |
| 96/19154 | 6/1996 | WIPO . |

*Primary Examiner*—John D. Yasko
*Attorney, Agent, or Firm*—Gerald W. Spinks

[57] ABSTRACT

A needle-less valve connector which employs a pre-slit elastomeric septum capable of axial movement proximally and distally within a housing. Connection of a blunt connector to the housing pushes the septum in the distal direction. A spring member biases the septum toward the proximal direction. The slit through the septum is held in the closed position, when the septum is in the proximal position, by an interference fit between the inside surface of the housing and the peripheral surface of the septum, with the interference fit causing an inward radial compression of the septum, orthogonal to the slit axis. The outer, or proximal, end surface of the septum can be shaped with a concave contour which causes the slit to completely close when the septum is in the proximal position. When a blunt connector is connected to the housing, the septum is pushed to a distal position, where other structure in the housing applies radial stress to the septum to open the slit. The axial locations of the housing structures which apply the radial loads to open and close the slit are selected to insure that the septum is sealed before the septum fully reaches the proximal position, thereby maintaining a seal between the blunt connector and the septum until after the slit is sealed. The structure which opens the slit is positioned to open the slit only after sufficient force is applied to the septum by the blunt connector, to insure that a seal exists between the blunt connector and the septum before opening of the slit.

23 Claims, 7 Drawing Sheet

U.S. PATENT DOCUMENTS

| | | | |
|---|---|---|---|
| 4,745,950 | 5/1988 | Mathieu | 137/798 |
| 4,752,287 | 6/1988 | Kurtz et al. | 604/99 |
| 4,752,292 | 6/1988 | Lopez et al. | 604/244 |
| 4,776,369 | 10/1988 | Lardner et al. | 137/515.5 |
| 4,786,281 | 11/1988 | Valentine et al. | 604/256 |
| 4,874,377 | 10/1989 | Newgard et al. | 604/167 |
| 5,006,114 | 4/1991 | Rogers et al. | 604/167 |
| 5,049,128 | 9/1991 | Duquette | 604/83 |
| 5,065,783 | 11/1991 | Ogle, II | 137/68.1 |
| 5,085,645 | 2/1992 | Purdy et al. | 604/167 |
| 5,147,333 | 9/1992 | Raines | 604/249 |
| 5,190,067 | 3/1993 | Paradis et al. | 137/1 |
| 5,201,725 | 4/1993 | Kling | 604/284 |
| 5,203,775 | 4/1993 | Frank et al. | 604/256 |
| 5,211,634 | 5/1993 | Vaillancourt | 604/167 |
| 5,215,538 | 6/1993 | Larkin | 604/249 |
| 5,230,706 | 7/1993 | Duquette | 604/83 |
| 5,242,393 | 9/1993 | Brimhall et al. | 604/86 |
| 5,242,432 | 9/1993 | DeFrank | 604/284 |
| 5,251,873 | 10/1993 | Atkinson et al. | 251/149.1 |
| 5,269,771 | 12/1993 | Thomas et al. | 604/213 |
| 5,273,533 | 12/1993 | Bonaldo | 604/83 |
| 5,295,657 | 3/1994 | Atkinson | 251/149.1 |
| 5,295,658 | 3/1994 | Atkinson et al. | 251/149.1 |
| 5,306,243 | 4/1994 | Bonaldo | 604/86 |
| 5,322,518 | 6/1994 | Schneider et al. | 604/247 |
| 5,342,326 | 8/1994 | Peppel et al. | 604/284 |
| 5,344,414 | 9/1994 | Lopez et al. | 604/283 |
| 5,353,837 | 10/1994 | Faust | 137/614.18 |
| 5,354,275 | 10/1994 | Behnke et al. | 604/86 |
| 5,360,413 | 11/1994 | Leason et al. | 604/249 |
| 5,390,898 | 2/1995 | Smedley et al. | 251/149.6 |
| 5,391,150 | 2/1995 | Richmond | 604/111 |
| 5,395,348 | 3/1995 | Ryan | 604/247 |
| 5,402,982 | 4/1995 | Atkinson et al. | 251/149.1 |
| 5,405,333 | 4/1995 | Richmond | 604/257 |
| 5,423,791 | 6/1995 | Bartlett | 604/403 |
| 5,439,451 | 8/1995 | Collinson et al. | 604/247 |
| 5,441,487 | 8/1995 | Vedder | 604/167 |
| 5,470,319 | 11/1995 | Mayer | 604/167 |
| 5,480,393 | 1/1996 | Bommarito | 604/283 |
| 5,487,728 | 1/1996 | Vaillancourt | 604/86 |
| 5,549,587 | 8/1996 | Siegel et al. | 604/256 |
| 5,569,235 | 10/1996 | Ross et al. | 604/403 |
| 5,676,346 | 10/1997 | Leinsing | 251/149 |

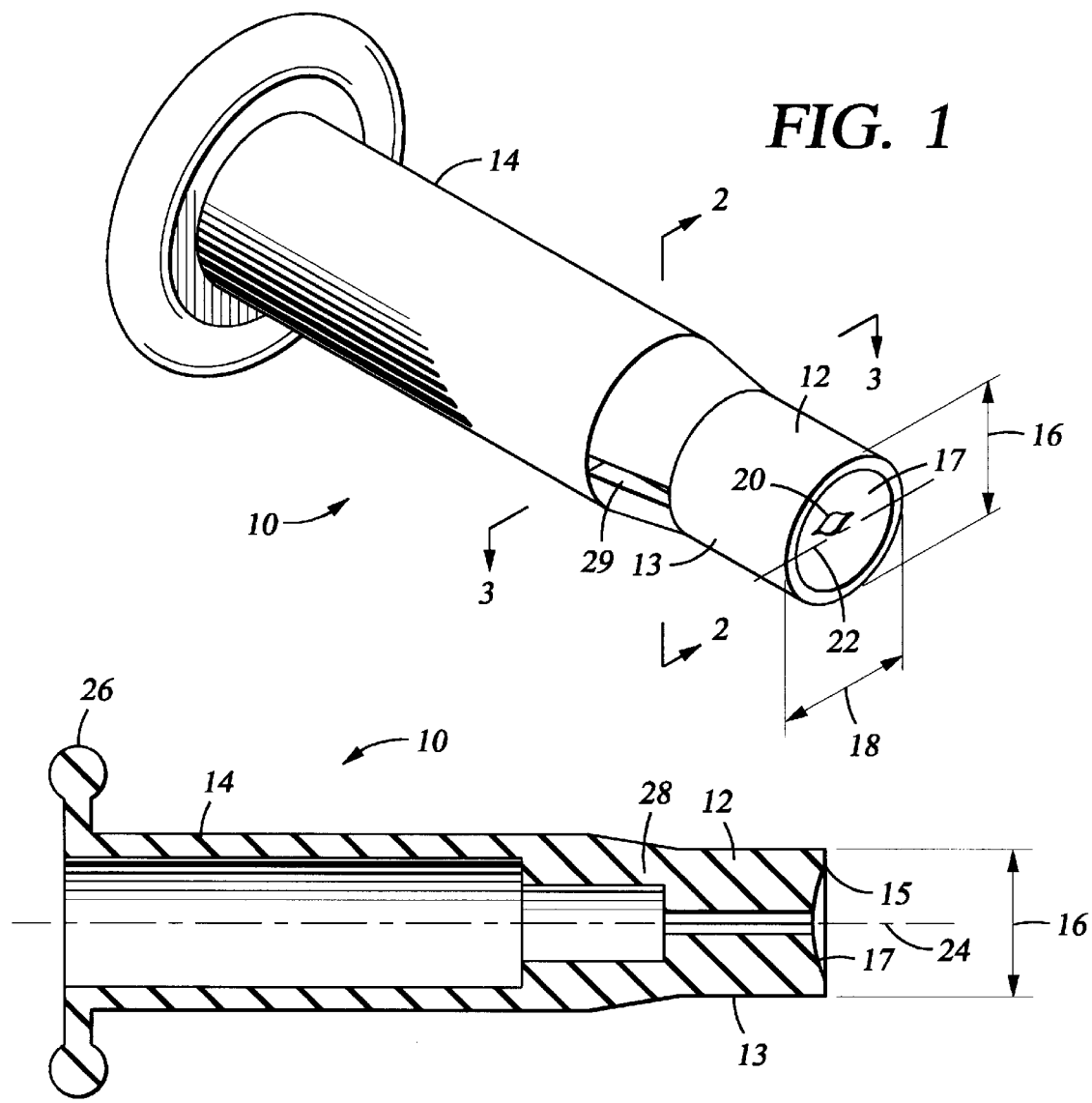
FIG. 1
FIG. 2
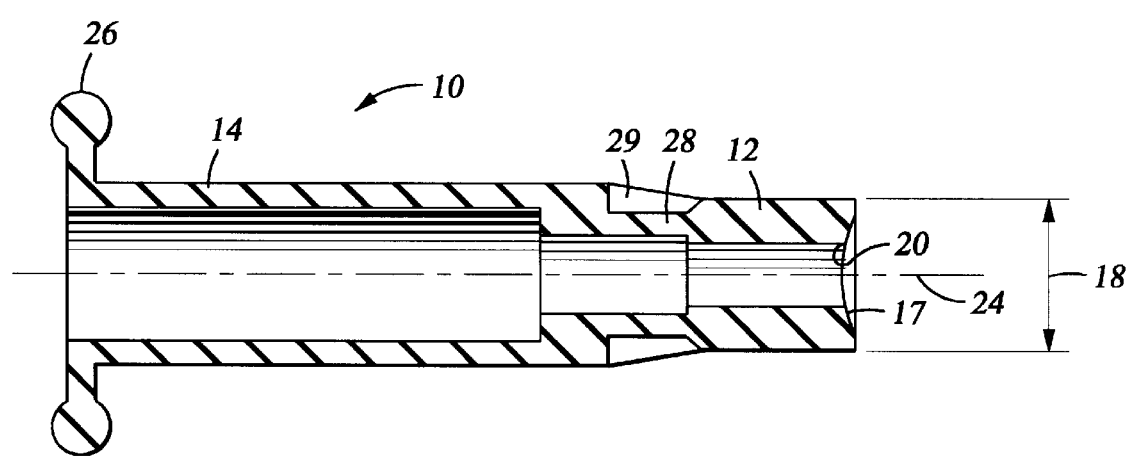
FIG. 3

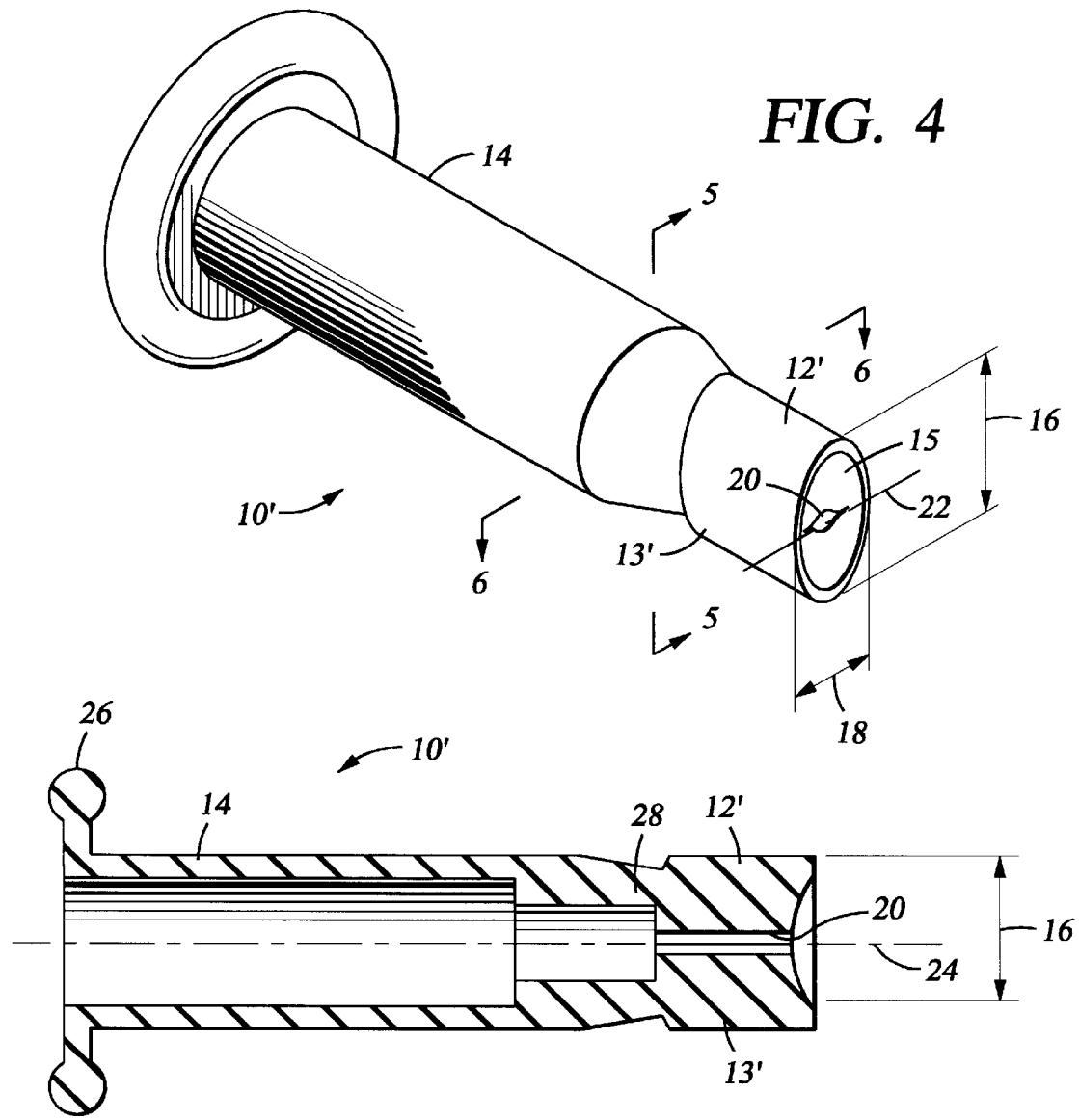
FIG. 4
FIG. 5
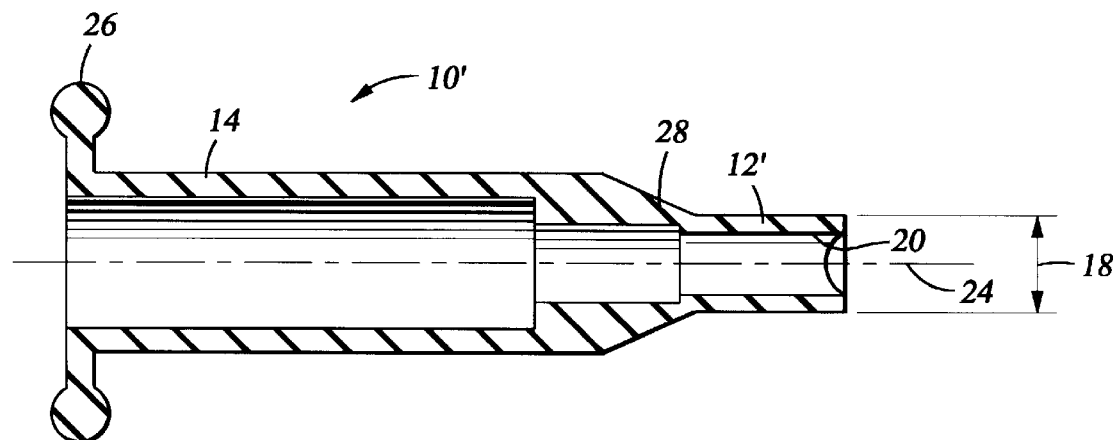
FIG. 6

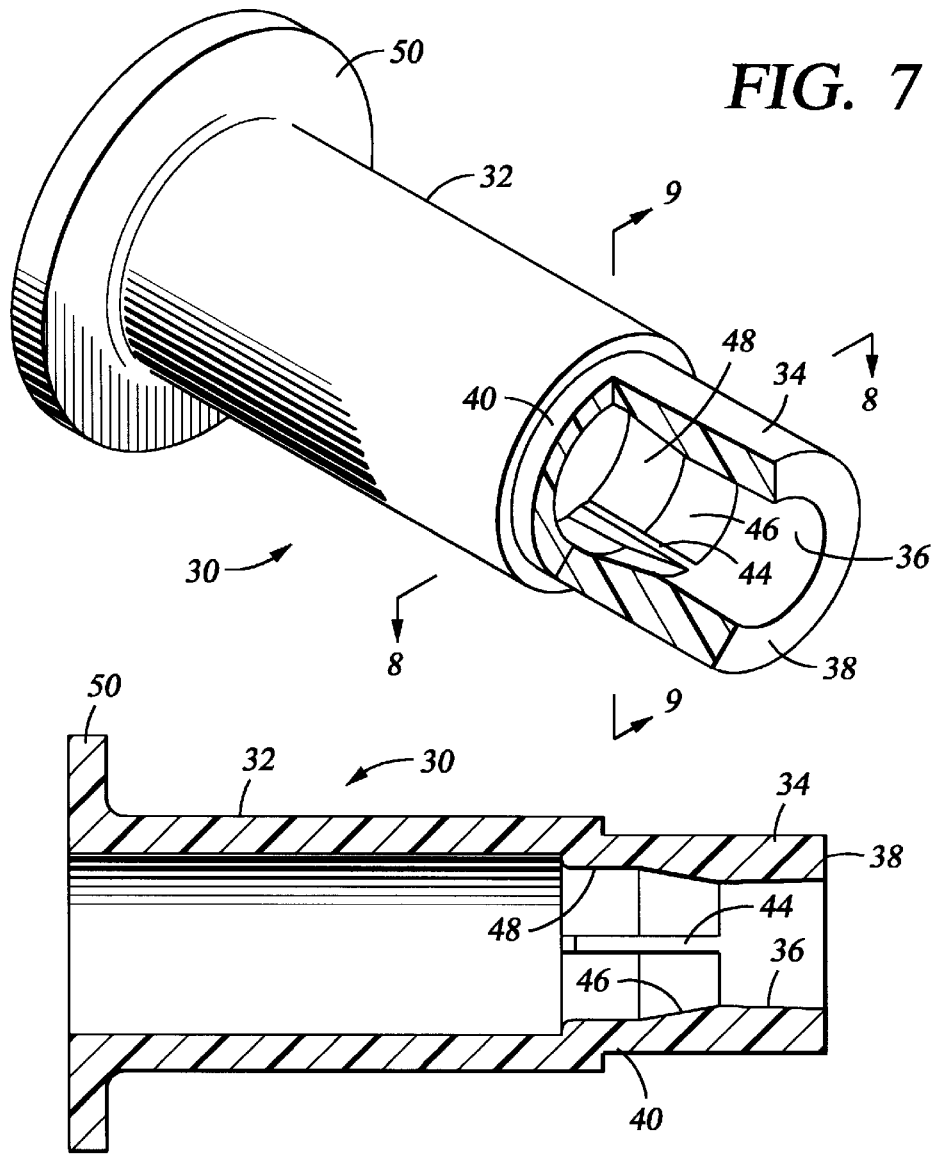
FIG. 7
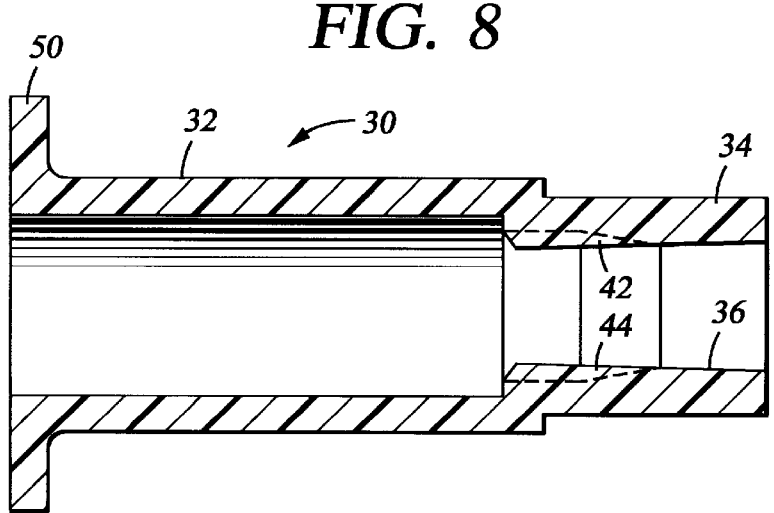
FIG. 8
FIG. 9

NEEDLELESS VALVE

CROSS REFERENCE TO RELATED APPLICATIONS

Not Applicable

FEDERALLY SPONSORED RESEARCH OR DEVELOPMENT

Not Applicable

BACKGROUND OF THE INVENTION

It is a well known practice to administer medications and other types of solutions to a patient with an intravascular administration set, consisting of a needle inserted into a blood vessel of the patient, flexible tubing connected to the needle, and various fittings for connecting fluid components to the flexible tubing. The fluid components can be a bottle of parenteral fluid, a bottle of a supplementary fluid, or a syringe of medication. Typically, one solution will be connected to flow continuously into the patient, while another solution will be added to the first solution at a branch connector located in the flexible tubing. Such connectors are often called "Y-sites". A Y-site is usually a sealed entry point having an elastomeric plug or septum. Medication can be introduced into the Y-site by injection through the elastomeric septum with a second needle, or by connecting a blunt connector to the Y-site, with flow through or past the septum being achieved by various means. Many connector devices in addition to the Y-site use the elastomeric septum for connection of fluid flow paths.

A major drawback of using a needle to penetrate the septum is that the use of sharp needles in any device frequently results in the occurrence of "needle stick" accidents, in which health care personnel are accidentally wounded by the needle. The needle stick accident can occur during insertion of the needle into the Y-site, or after use of the needle and before disposal. Needle stick accidents often spread infectious diseases, such as the HIV virus. This risk arises any time a sharp needle is used to connect two fluid flow components, not being restricted to the use of a Y-site in an I. V. set. Various devices have therefore been developed, which do not use a sharp needle, using instead a blunt device to connect to the Y-site or other connector. Most common among the "needle-less" connectors is the use of a luer connector, with an elastomeric septum in the female component, such as the Y-site, and a blunt male connector for connecting thereto. When the male luer connector is connected to the female luer connector, the septum is either pierced by a concealed piercing element, or the septum is otherwise penetrated or bypassed.

In a needle-less connector, there is typically a certain amount of dead space within the connector in which the septum is mounted, such as the Y-site. This allows for shifting or deformation of the septum, to achieve fluid flow. Unfortunately, dead space is undesirable, because it allows for the injection of air or contaminants into the patient along with the medication, accumulation of medication in a stagnant space, or coagulation of accumulated blood.

Further, needle-less connectors often allow the generation of a vacuum when the luer connector is disassembled. The vacuum results when a movable septum moves outwardly within the Y-site or other connector, upon disconnection, creating a lower than ambient pressure in the connector. If the septum is not sealed sufficiently to withstand the pressure differential before the connectors lose contact, flow from the ambient into the connector can occur. This vacuum can draw contaminants from the environment into the Y-site.

Another problem frequently associated with pre-slit needle-less connector devices is the failure of the opening in the septum to completely close at its outermost end, sometimes leaving a partially open slit in which contaminants can accumulate. Prior to use of the connector, it is common practice to wipe clean the exterior surface of the septum with alcohol, to remove contamination. However, if the septum has a slit which fails to completely close, the outer extremity of the slit can harbor contaminants which can not be effectively cleaned by wiping.

Finally, many known needle-less connectors suffer from the failure to seal against a required pressure differential. This can result from the absence of any structure in the housing to positively close the septum upon withdrawal of the blunt connector.

It is desirable, therefore, to have a needle-less connector which can be incorporated into a Y-site or any other type of fluid flow connector, which will limit the amount of dead space, counteract the formation of a vacuum, completely seal upon withdrawal of the associated connector, and effectively seal against significant pressure differentials.

BRIEF SUMMARY OF THE INVENTION

The present invention is a needle-less valve connector which employs a pre-slit elastomeric septum within a rigid housing such as a Y-site. The septum is capable of axial movement proximally and distally within the Y-site. Connection of a blunt connector, such as a male luer, to the female fitting on the Y-site pushes the septum in the distal direction. A spring member biases the septum toward the proximal direction. The slit through the septum is held in the closed position, when the septum is in the proximal position, by an interference fit between the inside surface of the housing and the peripheral surface of the septum, with the interference fit causing an inward radial compression of the septum, orthogonal to the slit axis. The interference fit must be sufficient to seal the slit against a pressure differential of at least 30 psi. The interference fit can be caused by using a septum having an elliptical cross section and a housing having a circular cross section, with the major axis of the septum being larger than the inside diameter of the housing. The major axis of the septum cross section would be orthogonal to the slit axis. Conversely, the septum could have a circular cross section, and the housing could be irregular or elliptical. In this type of device, the minor axis of the housing cross section would be positioned orthogonal to the slit axis in the septum. The outer, or proximal, end surface of the septum can be shaped with a concave contour which places the outer end of the slit at the axial location at which sufficient inward radial stress exists to completely close the slit when the septum is in the proximal position. This prevents the existence of a crevice at the outer extremity of the slit when the valve is closed.

When the blunt connector is connected to the valve, the septum is pushed to a distal position, where other structure in the housing applies radial stress to the septum to open the slit. This opening of the slit can be achieved in two ways. First, another interference fit between the inside surface of the housing and the peripheral surface of the septum can be used to apply inward radial stress to the septum, parallel to the slit axis, causing the slit to open as the septum moves in the distal direction. Here again, the septum could be irregularly shaped and the housing circular, or the septum could be circular and the housing irregular. Second, a hollow cannula in the distal end of the housing can be aligned with the slit to forcibly enter the distal end of the slit and apply outward radial stress to the septum, orthogonal to the slit axis, causing the slit to open as the septum moves in the distal direction. These two methods of applying radial stress to open the slit can be used separately, or in combination.

The axial locations of the housing structures which apply the radial loads to open and close the slit are selected to insure that the septum is sealed at all appropriate times. The structure which closes the slit is positioned to close and seal the slit before the septum fully reaches the proximal position, thereby maintaining a seal between the blunt connector and the septum until after the slit is sealed, preventing vacuum contamination. The structure which opens the slit is positioned to open the slit only after sufficient force is applied to the septum by the blunt connector, to insure that a seal exists between the blunt connector and the septum before opening of the slit.

The novel features of this invention, as well as the invention itself, will be best understood from the attached drawings, taken along with the following description, in which similar reference characters refer to similar parts, and in which:

BRIEF DESCRIPTION OF THE DRAWINGS

FIG. 1 is a perspective view of a first embodiment of an elliptical septum and a spring member according to the present invention, in the unconstrained condition;

FIG. 2 is a longitudinal section, orthogonal to the slit axis, of the septum shown in FIG. 1;

FIG. 3 is a longitudinal section, parallel to the slit axis, of the septum shown in FIG. 1;

FIG. 4 is a perspective view of a second embodiment of an elliptical septum and a spring member according to the present invention, with the septum having a higher aspect ratio between its major and minor axes;

FIG. 5 is a longitudinal section, orthogonal to the slit axis, of the septum shown in FIG. 4;

FIG. 6 is a longitudinal section, parallel to the slit axis, of the septum shown in FIG. 4;

FIG. 7 is a partial section of a first embodiment of a female valve connector housing according to the present invention, with wings projecting inwardly to apply inward radial stress to the septum in the distal position;

FIG. 8 is a longitudinal section, orthogonal to the plane of the wings, of the housing shown in FIG. 7;

FIG. 9 is a longitudinal section, parallel to the plane of the wings, of the housing shown in FIG. 7;

DETAILED DESCRIPTION OF THE INVENTION

Figure 10:
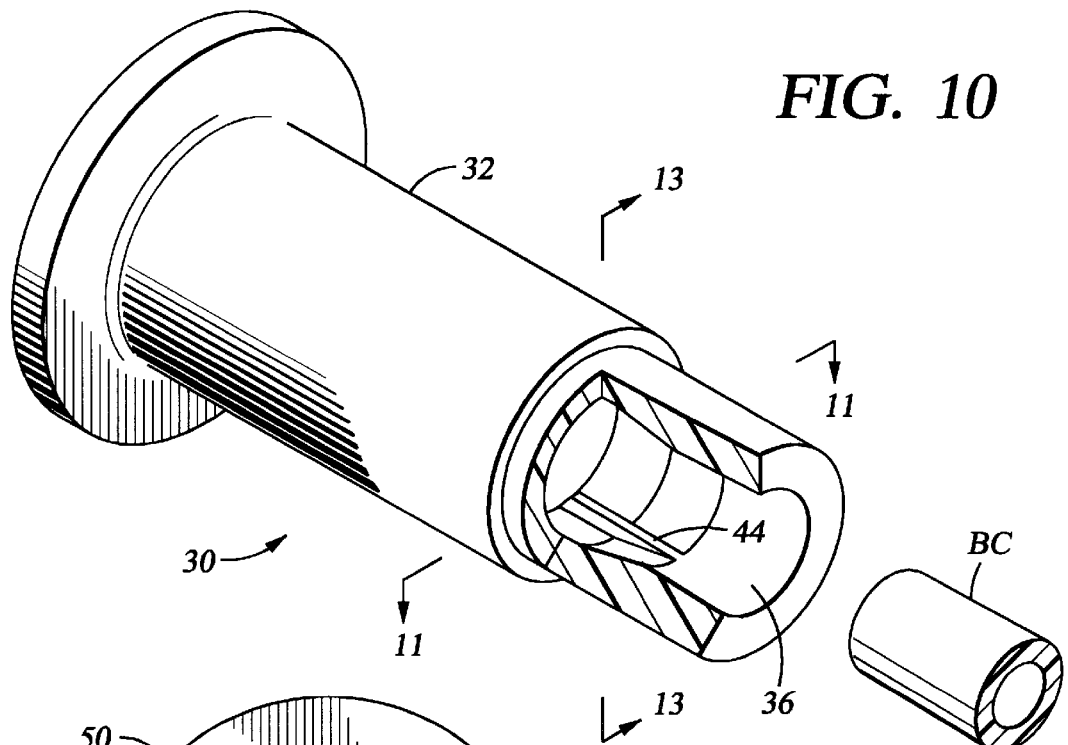
FIG. 10 is a partial section of the housing shown in FIG. 7, showing the introduction of a blunt connector.

FIG. 1 shows a hollow, combination elastomeric valve element 10 comprising a septum 12 and a spring element 14. In this view, the valve element 10 is in the unconstrained condition. The spring element can be a resilient elastomeric cylinder as shown, or it can be a spring, such as a coiled spring, in substantially the same location. If a coiled spring is used, it can be separate from the valve element 10 or integrated into the valve element 10. The septum 12 shown has an elliptical cross section, with a major transverse dimension, or major axis 16, and a minor transverse dimension, or minor axis 18. The septum 12 has a peripheral surface 13 and a proximal end surface 15. The septum 12 also could be another non-cylindrical shape without departing from the spirit of the invention. Further, depending upon the shape of other elements of the valve, the septum 12 could even have a cylindrical shape, as will be discussed later. A slit 20 is formed longitudinally through the septum 12. The cross section of the slit 20 can be a flat line, or slightly oval as shown, with a slit plane 22. The slit plane 22 is orthogonal to the major transverse dimension 16 of the septum 12. The end surface 15 has a concave surface 17 which ensures that the outer end of the slit 20 remains closed.

FIG. 2 shows a longitudinal cross section of the valve element 10, with the section being taken orthogonal to the slit plane 22. The longitudinal axis 24 of the valve element 10 can lie in the slit plane 22 as shown, or it can be offset therefrom. The valve element 10 also can have a sealing bead 26 near its distal end, to facilitate sealing the valve element to a housing, such as a Y-site. The configuration and location of the sealing member 26 can vary, to match the housing in which the valve element 10 is used. There can also be a tapered neck 28 in the valve element 10, to allow relative axial movement between the septum 12 and the remainder of the valve element 10. The neck 28 is also an alternative location for a spring element. The neck 28 can be provided with slots 29 to provide clearance for housing structure, as will be explained below. FIG. 3 shows another longitudinal cross section of the valve element 10, with the section being taken at, or in a plane parallel to, the slit plane 22. It can be seen from FIGS. 1 through 3 that the aspect ratio between the major transverse dimension 16 and the minor transverse dimension 18 of the septum 12 is not very much greater than unity, so the septum 12 is not far from being cylindrical in this embodiment.

FIG. 4 shows a second embodiment of the elastomeric valve element 10', with a septum 12' and a spring element 14. Here again, the slit plane 22 is orthogonal to the major transverse dimension 16 of the septum 12'. FIG. 5 shows a longitudinal cross section of the valve element 10', with the section being taken orthogonal to the slit plane 22. The slit plane 22 can contain the longitudinal axis 24 of the valve element 10, or it can be offset therefrom. FIG. 6 shows another longitudinal cross section of the valve element 10', with the section being taken at, or parallel to, the slit plane 22. In this embodiment, the aspect ratio between the major transverse dimension 16 and the minor transverse dimension 18 is much higher than in the first embodiment, making the septum 12' further from a cylindrical shape. A higher aspect ratio could be selected to apply higher radial stress to the septum 12, 12', or to provide more room for expansion of the minor transverse dimension 18 of the septum 12, 12'.

FIG. 7 shows a first embodiment of a rigid tubular connector housing 30 with which the valve element 10 can be used. The connector housing 30 includes generally a hollow, substantially cylindrical barrel 32 and a substantially cylindrical tubular valve housing 34 formed on a proximal end of the barrel 32. The connector housing 30 can also be fitted with a flange 50 for sealing against the sealing bead 26 of the valve element 10, if appropriate for the type of connector. The configurations shown for the distal ends of the connector housing 30 and the valve element 10, such as the flange 50 and the sealing element 26, are for illustration purposes only, with the actual configuration being adapted to the actual connector being designed. The tubular valve housing 34 has an inside surface 36 which interacts with the peripheral surface 13 of the septum 12, to place inward radial stress upon the septum 12 as desired to open or close the slit 20.

The interaction between the inside surface 36 of the valve housing 34 and the peripheral surface 13 of the septum 12 has two modes, one occurring when the septum 12 is positioned near the proximal end 38 of the valve housing 34 and the other occurring when the septum 12 is positioned near the distal end 40 of the valve housing 34. In this embodiment, the proximal portion of the inside surface 36 of the valve housing 34 has a circular cross section, as can be seen in FIGS. 8 and 9. The distal portion of the inside surface 36 of the valve housing 34 has two diametrically opposed inwardly sloping wings 42, 44. The distance between the wings 42, 44 is less than the internal diameter of the proximal portion of the valve housing 34, and less than the minor transverse dimension 18 of the septum 12. Except for the wings 42, 44, the internal surface 36 of the distal portion of the valve housing 34 has a conical surface 46 tapering outwardly to a larger diameter 48 at the proximal end 40. As mentioned above, instead of making the septum 12 with an elliptical cross section and the valve housing interior surface 36 with a circular cross section, the septum 12 could be circular and the valve housing 34 could be elliptical. Any such combination of corresponding shapes of the septum 12 and the valve housing 34 which results in an inward radial stress being placed on the septum 12 will comport with the spirit of the invention.

FIGS. 10 through 14 illustrate the interaction of the valve housing 34 and the septum 12, when assembled as a valve assembly 60. The particular valve housing 34 and septum 12 shown are chosen for illustration purposes only, to demonstrate the features of the present invention. Other appropriate shapes could be used as well, as long as they impose the radial stresses on the septum that are required for the present invention. The opening and closing of the slit 20 in the septum 12 are accomplished by moving the septum 12 axially within the valve housing 34, with movement of the septum 12 being accomplished by mating a blunt connector BC to the proximal end 38 of the valve housing 34, as shown in FIG. 10. For example, the proximal end 38 of the valve housing 34 could have a female luer fitting formed thereon, as is well known in the art, and the blunt connector BC could be found within a matching male luer connector. The spacing between the wings 42, 44 is designed to allow insertion of the blunt connector BC.

Figure 12:
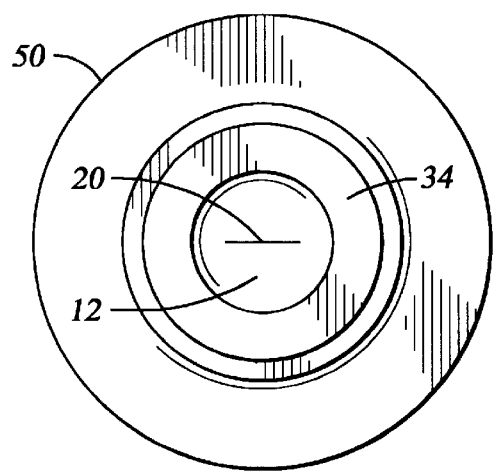
FIG. 12 is an end view of the valve assembly shown in FIG. 11.
Figure 11:
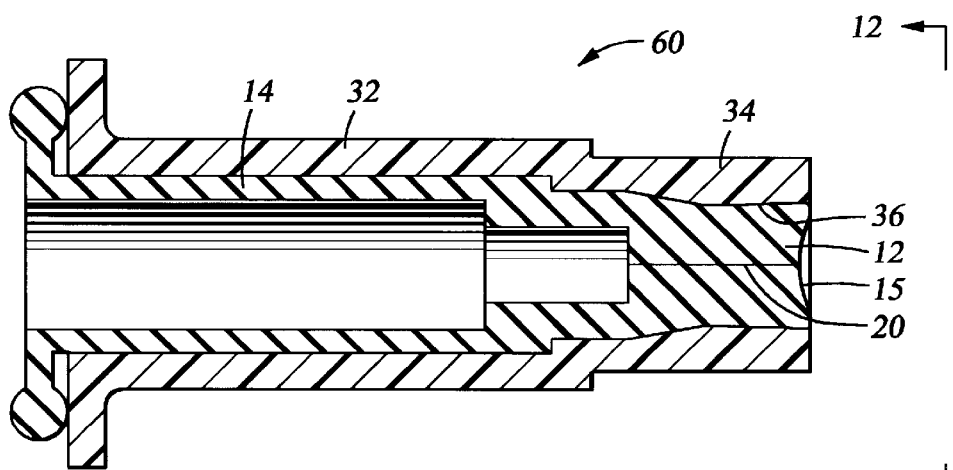
FIG. 11 is a longitudinal section, orthogonal to the plane of the wings and orthogonal to the slit axis, of the septum shown in FIG. 1 installed in the housing shown in FIG. 7, with the septum in the proximal position.

FIG. 11 shows the valve element 10 mated with the connector housing 30, with the septum 12 in the proximal position within the valve housing 34. The state shown is the normal disconnected state of the connector. The diameter of the proximal portion of the inside surface 36 of the valve housing 34 is smaller than the major transverse dimension 16 of the septum 12. This applies an inward radial compression to the septum 12 to close the slit 20, as seen in FIG. 12, against a pressure differential of at least 30 psi. When the apparatus is in the configuration shown in FIG. 12, the wings 42, 44 extend into the slots 29, so that the wings 42, 44 are not imposing a radial stress upon the septum 12. The proximal end surface 15 of the septum 12 preferably has a concave contour 17 shaped to ensure that the inward radial stress applied completely closes the slit, preventing the occurrence of a crevice.

Figure 13:
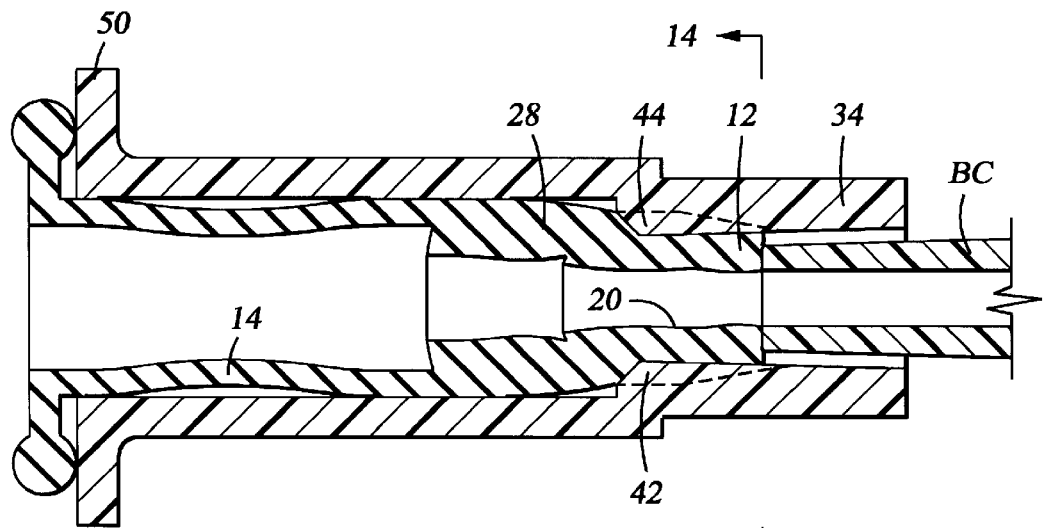
FIG. 13 is a longitudinal section, parallel to the plane of the wings and parallel to the slit axis, of the septum shown in FIG. 1 installed in the housing shown in FIG. 7, with the septum in the distal position.
Figure 14:
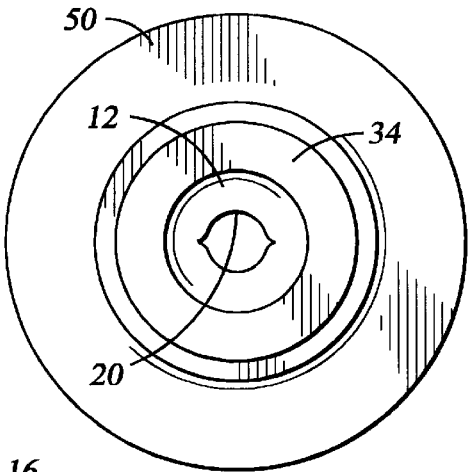
FIG. 14 is an end view of the valve assembly shown in FIG. 13.

As seen in FIG. 13, when the blunt connector BC is mated with the proximal end 38 of the valve housing 34, the septum 12 is pushed distally, partially compressing the spring element 14 and the valve neck 28. This places the septum 12 between the wings 42, 44, which are aligned with the slit plane 22. Since the space between the wings 42, 44 is smaller than the minor transverse dimension 18 of the septum 12, the wings 42, 44 impose inward radial stress on the septum 12 in line with the slit plane 22, causing the slit 20 to open as shown in FIG. 14. When the blunt connector BC is disconnected from the valve housing 34, the spring element 14 maintains the proximal end surface 15 of the septum 12 sealed against the blunt connector BC, until the septum 12 has re-entered the constriction at the proximal end of the valve housing 34. This insures that the slit 20 is closed and sealed before the blunt connector BC loses contact with the septum 12, preventing vacuum contamination of the valve assembly 60.

Figure 15:
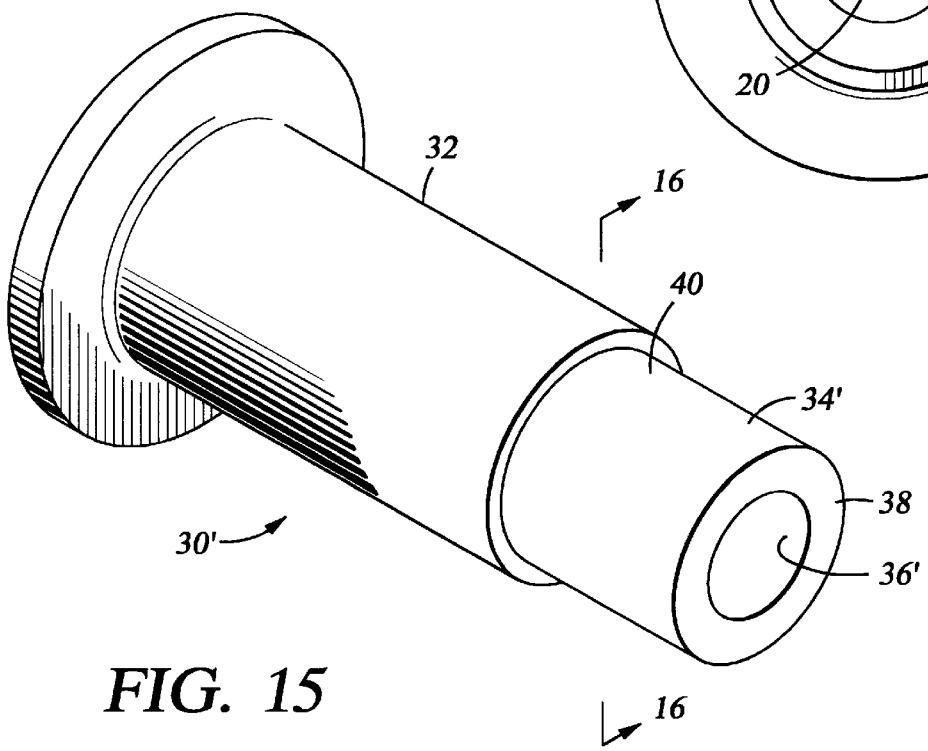
FIG. 15 is a perspective view of a second embodiment of a female valve connector housing according to the present invention.
Figure 16:
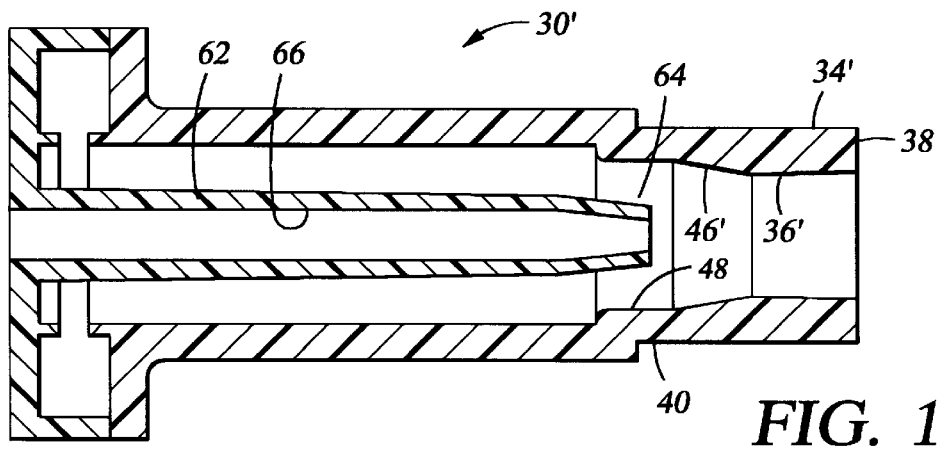
FIG. 16 is a longitudinal section of the housing shown in FIG. 15, with a blunt cannula projecting in the proximal direction.

FIGS. 15 and 16 show a second embodiment of a rigid tubular connector housing 30' with which the valve element 10, 10' can be used. The connector housing 30' includes generally a hollow, substantially cylindrical barrel 32 and a substantially cylindrical tubular valve housing 34' formed on a proximal end of the barrel 32. The tubular valve housing 34' has an inside surface 36' which interacts with the peripheral surface 13 of the septum 12, 12' to place inward radial stress upon the septum 12, 12' when the septum 12, 12' is in the proximal position, to close the slit 20.

The interaction between the inside surface 36' of the valve housing 34' and the peripheral surface 13 of the septum 12, 12' has two modes, one occurring when the septum 12, 12' is positioned near the proximal end 38 of the valve housing 34' and the other occurring when the septum 12, 12' is positioned near the distal end 40 of the valve housing 34'. The proximal portion of the inside surface 36' of the valve housing 34' has a circular cross section. The valve housing 34' is different from the first embodiment, in that it has no wings 42, 44. The internal surface 36' of the distal portion of the valve housing 34' has a conical surface 46' tapering outwardly to a larger diameter 48 at the proximal end 40. Opening of the slit 20 is accomplished by a hollow rigid cannula 62 mounted to the flange 50 by means such as solvent bonding, and extending proximally within the barrel 32. The cannula 62 extends proximally into the distal portion of the valve housing 34'. The proximal end 64 of the cannula 62 aligns with the slit 20 of the septum 12, 12'. As mentioned before, instead of making the septum 12, 12' with an elliptical cross section and the valve housing interior surface 36' with a circular cross section, the septum 12, 12' could be circular and the valve housing 34' could be elliptical. Any such combination of corresponding shapes of the septum 12, 12' and the valve housing 34' which results in an inward radial stress being placed on the septum 12, 12' will comport with the spirit of the invention.

Figure 17:
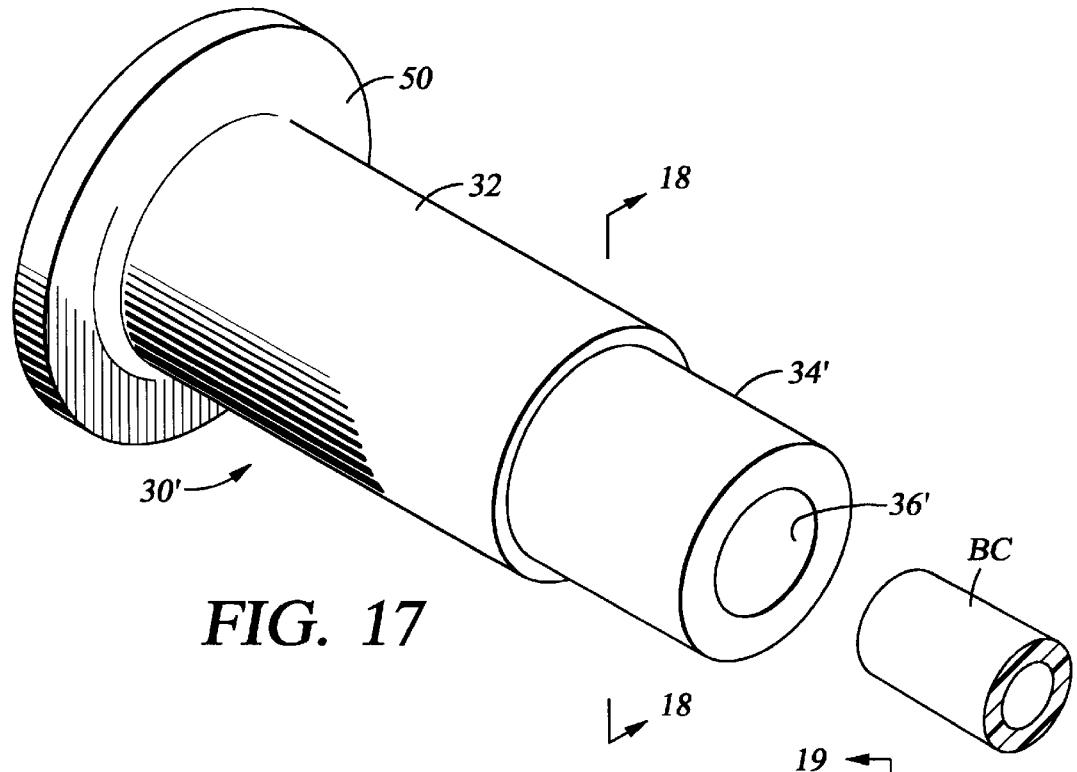
FIG. 17 is a perspective view of the housing shown in FIG. 15, showing the introduction of a blunt connector.

FIGS. 17 through 21 illustrate the interaction of the valve housing 34' and the septum 12' when assembled as a valve assembly 60'. The particular valve housing 34' and septum 12' shown are chosen for illustration purposes only, to demonstrate the features of the present invention. Other appropriate shapes could be used as well, as long as they impose the radial stresses on the septum that are required for the present invention. The opening and closing of the slit 20 in the septum 12' are accomplished by moving the septum 12' axially within the valve housing 34', with movement of the septum 12' being accomplished by mating a blunt connector BC to the proximal end 38 of the valve housing 34', as shown in FIG. 17. For example, the proximal end 38 of the valve housing 34' could have a female luer fitting formed thereon, as is well known in the art, and the blunt connector BC could be found within a matching male luer connector. The internal diameter of the surface 36' is designed to allow insertion of the blunt connector BC.

Figure 18:
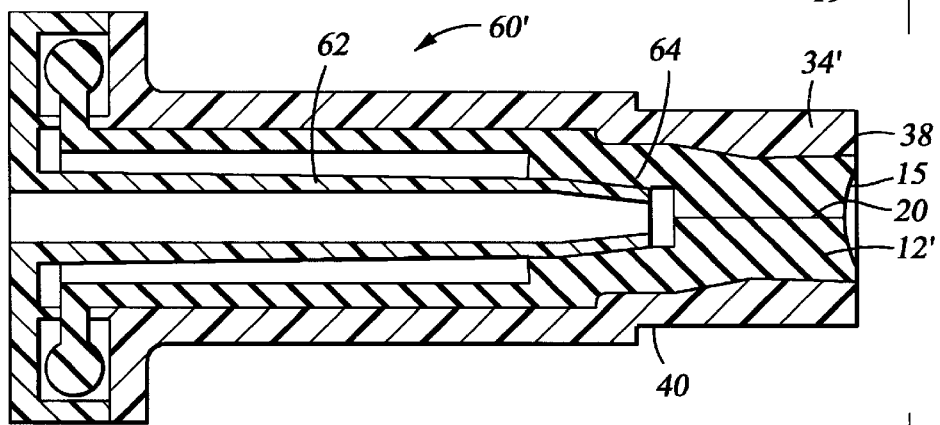
FIG. 18 is a longitudinal section of the septum shown in FIG. 4 installed in the housing shown in FIG. 15, with the septum in the proximal position.
Figure 19:
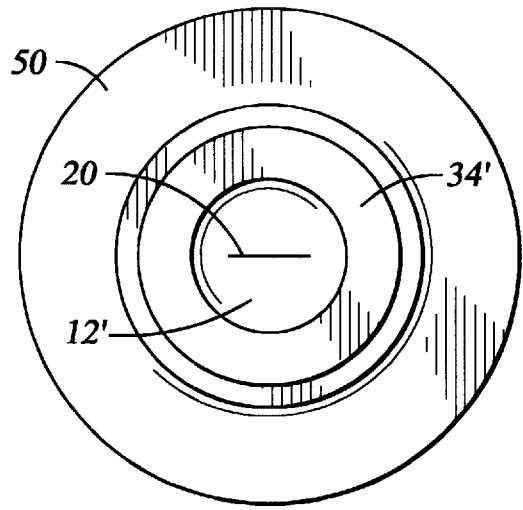
FIG. 19 is an end view of the valve assembly shown in FIG. 18.

FIG. 18 shows the valve element 10' mated with the connector housing 30', with the septum 12' in the proximal position within the valve housing 34'. Valve element 10 could also be used. The state shown is the normal disconnected state of the connector. The diameter of the proximal portion of the inside surface 36' of the valve housing 34' is smaller than the major transverse dimension 16 of the septum 12'. This applies an inward radial compression to the septum 12' to close the slit 20, as seen in FIG. 19. The proximal end surface 15 of the septum 12' preferably has a concave contour shaped to insure that the inward radial stress applied completely closes the slit, preventing the occurrence of a crevice.

Figure 20:
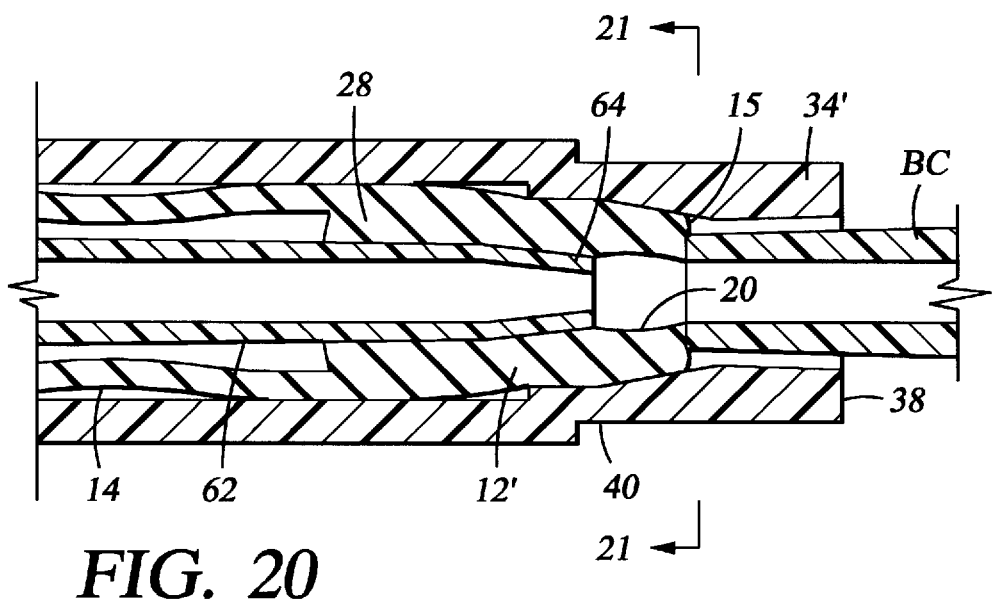
FIG. 20 is a longitudinal section of the septum shown in FIG. 4 installed in the housing shown in FIG. 15, with the septum in the distal position.
Figure 21:
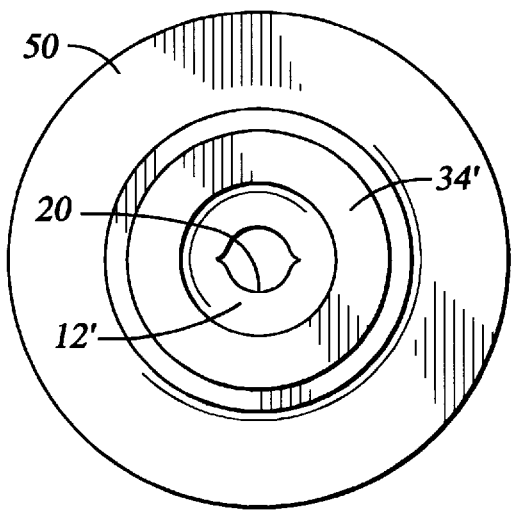
FIG. 21 is an end view of the valve assembly shown in FIG. 20.

As seen in FIG. 20, when the blunt connector BC is mated with the proximal end 38 of the valve housing 34', the septum 12' is pushed distally, partially compressing the spring element 14 and the valve neck 28. This causes the septum 12' to contact the proximal end 64 of the hollow cannula 62. As the hollow cannula 62 enters the slit 20, it imposes outward radial stress on the septum 12', causing the slit 20 to open as shown in FIG. 21. It is important to note that internal contours of the valve housing 34' and the axial position of the proximal end 64 of the cannula are designed so that the proximal end 64 of the cannula 62 does not extend far enough in the proximal direction to contact the blunt cannula BC when the blunt cannula BC has been inserted completely into the connector housing 30'. This is because, even though the length, taper angle, and outside diameter of the blunt connector BC are controlled by industry standards, the internal diameter of the blunt connector BC is not a controlled dimension.

When the blunt connector BC is disconnected from the valve housing 34', the spring element 14 maintains the proximal end surface 15 of the septum 12' sealed against the blunt connector BC, until the septum 12' has re-entered the constriction at the proximal end of the valve housing 34'. This insures that the slit 20 is closed and sealed before the blunt connector BC loses contact with the septum 12', preventing vacuum contamination of the valve assembly 60'.

While the particular invention as herein shown and disclosed in detail is fully capable of obtaining the objects and providing the advantages hereinbefore stated, it is to be understood that this disclosure is merely illustrative of the presently preferred embodiments of the invention and that no limitations are intended other than as described in the appended claims.

We claim:

1. A valve assembly for connecting intravascular fluid flow components, said valve assembly comprising:

a substantially tubular housing;

a compressible elastomeric septum slidably disposed within said tubular housing for axial movement between a proximal position and a distal position of said septum;

a spring element for biasing said septum from said distal position to said proximal position;

a slit formed axially through said septum;

a first radial loading contour within said tubular housing for applying substantially radial compressive force to a first transverse dimension of said septum when said septum is in said proximal position, to hold said slit in a closed state; and a second radial loading contour within said tubular housing for applying substantially radial force to a second transverse dimension of said septum when said septum is in said distal position, to hold said slit in an open state;

wherein said septum is slidable from said proximal position to said distal position by axial force exerted by a fluid fitting being connected to a proximal portion of said tubular housing.

2. A valve assembly as claimed in claim 1, further comprising a substantially concave contour formed on a proximal surface of said septum, wherein said concave contour on said septum and said first radial loading contour within said housing are constructed and axially located so as to close said slit at a proximal end of said slit, and to seal said slit against a selected pressure differential at an intermediate depth within said slit.

3. A valve assembly as claimed in claim 2, wherein said first radial loading contour seals said slit against a pressure differential of at least 30 psi.

4. A valve assembly as claimed in claim 1, wherein said first radial loading contour is formed on an inner wall of said tubular housing, said first loading contour having a transverse dimension less than said first transverse dimension of said septum, said first transverse dimension of said septum being orthogonal to said slit, said transverse dimension of said first loading contour aligning with said first transverse dimension of said septum when said septum is in said proximal position, thereby compressing said first transverse dimension of said septum from a first value to a smaller second value, to close said slit.

5. A valve assembly as claimed in claim 4, wherein said first loading contour on said inner wall of said tubular housing comprises a substantially circular contour, said circular contour creating a circular lumen having a diameter less than said first transverse dimension of said septum.

6. A valve assembly as claimed in claim 4, wherein said first loading contour on said inner wall of said tubular housing comprises an inwardly projecting contour, said inwardly projecting contour creating a non-circular lumen having a transverse dimension less than said first transverse dimension of said septum.

7. A valve assembly as claimed in claim 4, wherein said septum has a circular cross section at said first transverse dimension.

8. A valve assembly as claimed in claim 4, wherein said septum has a non-circular cross section at said first transverse dimension.

9. A valve assembly as claimed in claim 1, wherein said second radial loading contour comprises a second contour on an inner wall of said tubular housing, said second loading contour having a transverse dimension less than said second transverse dimension of said septum, said second transverse dimension of said septum being parallel to said slit, said transverse dimension of said second loading contour aligning with said second transverse dimension of said septum when said septum is in said distal position, thereby applying an inward radial force compressing said second transverse dimension of said septum from a first value to a smaller second value, to open said slit.

10. A valve assembly as claimed in claim 9, wherein said second loading contour on said inner wall of said tubular housing comprises a substantially circular contour, said circular contour creating a circular lumen having a diameter less than said second transverse dimension of said septum.

11. A valve assembly as claimed in claim 9, wherein said second loading contour on said inner wall of said tubular housing comprises an inwardly projecting contour, said inwardly projecting contour creating a non-circular lumen having a transverse dimension less than said second transverse dimension of said septum.

12. A valve assembly as claimed in claim 9, wherein said septum has a circular cross section at said second transverse dimension.

13. A valve assembly as claimed in claim 9, wherein said septum has a non-circular cross section at said second transverse dimension.

14. A valve assembly as claimed in claim 1, wherein:
said second radial loading contour comprises a cannula formed within a distal portion of said tubular housing;
said cannula has a proximal end substantially aligned with said slit to cause said cannula to enter said slit when said septum moves to said distal position, thereby applying an outward radial force to said septum, to open said slit; and
said proximal end of said cannula extends only partially through said slit when said septum is in said distal position.

15. A valve assembly as claimed in claim 1, wherein said first radial loading contour on an inner wall of said tubular housing and said first transverse dimension of said septum are formed at relative axial positions which result in said application of said compressive force to said septum through a finite range of axial movement of said septum, thereby closing said slit as said septum moves from said distal position toward said proximal position while said spring element still maintains a sealing engagement between a proximal surface of said septum and a fitting being disconnected from said proximal portion of said tubular housing, and thereby maintaining said slit in a closed state as said septum moves from said proximal position toward said distal position until said spring element achieves a sealing engagement between said proximal surface of said septum and a fitting being connected to said proximal portion of said tubular housing.

16. A valve assembly for connecting intravascular fluid flow components, said valve assembly comprising:
a substantially tubular housing;
a compressible elastomeric septum slidably disposed within said tubular housing for axial movement between a proximal position and a distal position of said septum, said septum having a non-circular transverse cross section with a major axis and a minor axis;
a spring element for biasing said septum from said distal position to said proximal position;
a slit formed axially through said septum, said slit being orthogonal to said major axis of said septum;
a substantially circular loading contour formed on an inner wall of said tubular housing, said circular loading contour having a diameter less than said major axis of said septum, said loading contour aligning with said major axis of said septum when said septum is in said proximal position, for applying substantially radial force to compress said major axis of said septum from a first value to a smaller second value, to close said slit; and
a cannula formed within a distal portion of said tubular housing, said cannula having a proximal end substantially aligned with said slit to cause said cannula to enter said slit when said septum moves to said distal position, thereby applying an outward radial force to said septum, to open said slit, said proximal end of said cannula extending only partially through said slit when said septum is in said distal position;
wherein said septum is slidable from said proximal position to said distal position by axial force exerted by a fluid fitting being connected to a proximal portion of said tubular housing.

17. A valve assembly as claimed in claim 16, further comprising a substantially concave contour formed on a proximal surface of said septum, wherein said concave contour on said septum and said loading contour within said housing are constructed and axially located so as to close said slit at a proximal end of said slit, and to seal said slit against a selected pressure differential at an intermediate depth within said slit.

18. A valve assembly as claimed in claim 17, wherein said loading contour seals said slit against a pressure differential of at least 30 psi.

19. A valve assembly as claimed in claim 16, wherein said loading contour within said tubular housing and said major axis of said septum are formed at relative axial positions which result in said application of said compressive force to said septum through a finite range of axial movement of said septum, thereby closing said slit as said septum moves from said distal position toward said proximal position while said spring element still maintains a sealing engagement between a proximal surface of said septum and a fitting being disconnected from said proximal portion of said tubular housing, and thereby maintaining said slit in a closed state as said septum moves from said proximal position toward said distal position until said spring element achieves a sealing engagement between said proximal surface of said septum and a fitting being connected to said proximal portion of said tubular housing.

20. A valve assembly for connecting intravascular fluid flow components, said valve assembly comprising:
a substantially tubular housing;
a compressible elastomeric septum slidably disposed within said tubular housing for axial movement between a proximal position and a distal position of said septum, said septum having a substantially circular transverse cross section;
a spring element for biasing said septum from said distal position to said proximal position;
a slit formed axially through said septum;
a first inwardly projecting loading contour formed on an inner wall of said tubular housing, said first loading contour creating a non-circular lumen having a transverse dimension less than the diameter of said septum, said first loading contour aligning with said septum when said septum is in said proximal position, for applying substantially radial force to compress a first transverse dimension of said septum, to close said slit; and a second inwardly projecting loading contour formed on said inner wall of said tubular housing, said second loading contour creating a non-circular lumen having a transverse dimension less than the diameter of said septum, said second loading contour aligning with said septum when said septum is in said distal position, for applying substantially radial force to compress a second transverse dimension of said septum, to open said slit;

wherein said septum is slidable from said proximal position to said distal position by axial force exerted by a fluid fitting being connected to a proximal portion of said tubular housing.

21. A valve assembly as claimed in claim 20, further comprising a substantially concave contour formed on a proximal surface of said septum, wherein said concave contour on said septum and said first loading contour within said housing are constructed and axially located so as to close said slit at a proximal end of said slit, and to seal said slit against a selected pressure differential at an intermediate depth within said slit.

22. A valve assembly as claimed in claim 21, wherein said first loading contour seals said slit against a pressure differential of at least 30 psi.

23. A valve assembly as claimed in claim 20, wherein said first loading contour within said tubular housing and said diameter of said septum are formed at relative axial positions which result in said application of said compressive force to said septum through a finite range of axial movement of said septum, thereby closing said slit as said septum moves from said distal position toward said proximal position while said spring element still maintains a sealing engagement between a proximal surface of said septum and a fitting being disconnected from said proximal portion of said tubular housing, and thereby maintaining said slit in a closed state as said septum moves from said proximal position toward said distal position until said spring element achieves a sealing engagement between said proximal surface of said septum and a fitting being connected to said proximal portion of said tubular housing.

* * * * *